(12) United States Patent
Padala et al.

(10) Patent No.: US 9,662,208 B2
(45) Date of Patent: May 30, 2017

(54) DEVICES AND METHODS FOR SURGICAL AND PERCUTANEOUS REPAIR OF HEART VALVE LESIONS

(75) Inventors: Saimuralidhar Padala, Atlanta, GA (US); Vinod H. Thourani, Atlanta, GA (US)

(73) Assignee: Emory University, Atlanta, GA (US)

( * ) Notice: Subject to any disclaimer, the term of this patent is extended or adjusted under 35 U.S.C. 154(b) by 34 days.

(21) Appl. No.: 13/978,904

(22) PCT Filed: Jan. 25, 2012

(86) PCT No.: PCT/US2012/022487
§ 371 (c)(1),
(2), (4) Date: Oct. 7, 2013

(87) PCT Pub. No.: WO2012/103173
PCT Pub. Date: Aug. 2, 2012

(65) Prior Publication Data
US 2014/0039615 A1     Feb. 6, 2014

Related U.S. Application Data

(60) Provisional application No. 61/436,065, filed on Jan. 25, 2011.

(51) Int. Cl.
A61F 2/24 (2006.01)

(52) U.S. Cl.
CPC ............ *A61F 2/2445* (2013.01); *A61F 2/246* (2013.01); *A61F 2/2454* (2013.01); *A61F 2/2457* (2013.01); *A61F 2250/0003* (2013.01)

(58) Field of Classification Search
USPC ............ 623/1.24–1.26, 2.11–2.19, 2.36–2.41
See application file for complete search history.

(56) References Cited

U.S. PATENT DOCUMENTS

| | | | |
|---|---|---|---|
| 8,460,370 B2 | 6/2013 | Zakay et al. | |
| 2003/0083742 A1 | 5/2003 | Spence et al. | |
| 2004/0127982 A1 | 7/2004 | Machold et al. | |
| 2004/0138745 A1* | 7/2004 | Macoviak ............... A61B 19/26 | 623/2.36 |
| 2005/0004665 A1 | 1/2005 | Aklog | |
| 2005/0004668 A1* | 1/2005 | Aklog et al. .................. 623/2.36 | |
| 2005/0038508 A1 | 2/2005 | Gabbay | |
| 2005/0070999 A1* | 3/2005 | Spence .................. A61F 2/2418 | 623/2.37 |
| 2006/0229708 A1 | 10/2006 | Powell et al. | |
| 2008/0125860 A1 | 5/2008 | Webler et al. | |
| 2010/0076550 A1 | 3/2010 | Subramanian | |
| 2010/0262233 A1 | 10/2010 | He | |
| 2010/0298929 A1 | 11/2010 | Thornton et al. | |
| 2010/0318184 A1 | 12/2010 | Spence | |

* cited by examiner

*Primary Examiner* — Yashita Sharma
(74) *Attorney, Agent, or Firm* — Emory Patent Group

(57) ABSTRACT

The devices and methods relate to surgical and percutaneous repair of heart valve regions. The devices may be structured to conform to the desired shape of a specific patient. The devices may include a frame and an artificial body onto which leaflets of the valve may coapt or rest.

20 Claims, 13 Drawing Sheets

DEVICES AND METHODS FOR SURGICAL AND PERCUTANEOUS REPAIR OF HEART VALVE LESIONS

CROSS REFERENCE TO RELATED APPLICATIONS

This application claims priority to U.S. Provisional Application Ser. No. 61/436,065 filed Jan. 25, 2011, which is hereby incorporated by this reference in its entirety.

FIELD

This disclosure relates to devices and methods for surgical and percutaneous repair of heart valve lesions. In some embodiments, the disclosure relates to devices having a frame and a bridge that is structured to be adjusted according to the anatomy of a patient's valve. The devices may include a frame and an artificial body onto which leaflets of the valve may coapt or rest. The devices may include an annular ring. The devices may include a frame and an artificial body onto which leaflets of the valve may coapt or rest. The devices may further include an annular ring.

BACKGROUND

Heart valve disorders rank second in all cardiovascular diseases that contribute to mortality in the western and eastern worlds, and impose significant financial burden on healthcare systems. Currently, patients receive either medical treatment or surgical repair or replacement of diseased heart valve(s) using open heart surgery. Medical treatment is only a medical management option that reduces the symptoms in these patients. However, medical treatment typically only delays the need for surgery. Most patients require surgery at some point in their life. In patients who receive surgery, traditional methods of surgery use either mechanical or bio-prosthetic replacement valves in place of native diseased valves, or the native diseased valve is repaired or corrected by manipulating the native valve tissue.

Valve replacement, however, has its drawbacks and has been losing traction as the standard of care. Valve replacement requires lifelong anti-coagulation therapy with mechanical heart valves, and has less than 10 years of durability with the use of bio-prosthetic heart valves.

Valve repair, on the other hand, is becoming more popular as the standard of care. Up to 250,000 valve repair procedures are performed each year in the United States alone. However, the durability of such repairs has been very sub-optimal with persistent or recurrent valve regurgitation occurring in up to 64% of the patients. Valve repair procedures typically fail because of the inflexibility of current valve repair devices, specifically, the inability of the procedure to address different valve defects on a patient specific basis. Also, the procedure to implant current devices requires arresting the heart, assessing the appropriate device shape and size on a flaccid (non-beating) heart, closing the heart and chest via incisions, and then recovering the patient from cardiopulmonary bypass and anesthesia to assess if the valve repair was successful. Patients often have persistent or recurrent valve leakage when the heart resumes beating, even though complete elimination of regurgitation at the time of the valve surgery on the flaccid heart may have been observed. Thus, such patients present with regurgitation after valve repair surgery and often do not receive any additional care because a second surgery would increase the risk of mortality.

There are valve repair devices and methods that are designed to treat regurgitation. See, e.g., U.S. patent application Ser. No. 12/858,935 filed Apr. 18, 2010 (Spence), U.S. patent application Ser. No. 12/626,272 filed Nov. 25, 2009 (Subramanian), U.S. patent application Ser. No. 12/422,287 filed Apr. 12, 2009 (He), and U.S. patent application Ser. No. 12/761,225 filed Apr. 15, 2010 (Zakay et al.). However, these devices are not structured to be adjusted and adapted to different valve defects on a patient specific basis.

Thus, there is a need for valve repair devices and methods that address the patient variability in heart valve structure and function. Specifically, there is a need for beating heart adjustable devices that conform to the desired shape in individual patients at the time of surgery, or acutely after surgery or several years after surgery.

SUMMARY

The disclosure relates to devices and methods for surgical and percutaneous repair of heart valve regions. In some embodiments, the disclosure may relate to a device for repairing a heart valve having native valve leaflets. The device may include an artificial body having a surface structured to receive the native valve leaflets; and a frame. In some embodiments, the frame may be structured to adjust to a shape of the heart valve, wherein the artificial body is structured to be mounted onto the frame, and wherein the frame is structured to be inserted onto the heart valve in a desired configuration so as to eliminate leakage of blood through the valve due to lack of coaptation or overlap between the valve leaflets.

In some embodiments, the devices may include a coaptation member. The coaptation member may include a bridge onto which the artificial body may be fixedly disposed. The bridge may have an even curvature. In other embodiments, the bridge may have an uneven curvature. The shape of the bridge may depend on the anatomy of the valve. The bridge may be different for the atrioventricular and semilunar valves.

In some embodiments, the surface may be structured so that when the artificial body is implanted, the native valve leaflets coapt or rest on the artificial body during closure of the valve. In some embodiments, the artificial body may include an inflatable member. The inflatable member may be structured to be adjustable upon implantation in the heart valve. The size and shape of the inflatable member may be adjustable upon implantation in the heart valve. In some embodiments, size and shape of the artificial body may depend on anatomy of heart valve. In further embodiments, the size and shape of the artificial body may depend on intended placement of the artificial body in the heart valve. In further embodiments, the surface may be structured to extend along the entire length of overlap between the leaflets or only a section of a length of the leaflet coaptation.

In some embodiments, the frame may be structured to be inserted onto the heart valve in a desired configuration so as to eliminate leakage of blood through the valve due to lack of coaptation or overlap between the valve leaflets.

In further embodiments, the device may include an annular ring, wherein the frame is made of a shape forming alloy material, and wherein the frame includes multiple curved elements originating from the artificial body and ending in the annular ring.

In some embodiments, the frame may include multiple grooves on the frame structured to mount the artificial bodies at selected locations on the frame. In further embodiments, the combination of the artificial body and the frame may be structured to control a leaflet of the valve from prolapsing and adjust combination to a configuration such that the at least one leaflet may overlap on the artificial body.

In other embodiments, the artificial body may be structured to have an adjustment of a depth or distance from an annulus of the valve when implanted. In other embodiments, the artificial body may include a curvature, the amount of curvature depending on the desired depth or distance from an annulus of the valve when implanted.

In further embodiments, the device may further include another frame. The another frame may be an annular ring, wherein the artificial body ends in the annular ring. In other embodiments, the frame and artificial body may be structured to be directly mounted onto annulus of the valve or on a previously implanted annuloplasty ring. In some embodiments, the device may be without an annular ring.

In other embodiments, the disclosure relates to a device for repairing a heart valve of a patient having native valve leaflets. The device may include an artificial body having a surface structured to receive the native valve leaflets; wherein the artificial body is structured to be mounted onto a frame that is structured to hold the artificial body in the implanted configuration for duration that the frame remains in the heart. In some embodiments, the artificial body may be structured to be implanted onto a frame previously implanted into the heart.

In some embodiments, the disclosure relates to a surgical implant device for a heart valve of a patient. The device may include a frame; and a coaptation member, wherein the coaptation member is structured to be adjusted to correspond to an anatomy of the valve of the patient. In other embodiments, the coaptation member may include a bridge. The coaptation member may include at least one artificial body. The artificial body may include at least one inflatable member, the inflatable member being structured to be adjustable to correspond to the anatomy of valve. In some embodiments, the coaptation member may include three inflatable members. In further embodiments, the inflatable members may be structured to be inflated individually. In other embodiments, the frame may include a mechanism that is structured to inflate the inflatable members. In some embodiments, the frame may be structured to expand and collapse. In some embodiments, the bridge may extend from one side of the frame to an opposing side.

In some embodiments, the disclosure may relate to kits. The kits may be sterilized and configured for single use. The kit may include at least one frame and a coaptation member. In some embodiments, the kit may include a plurality of different coaptation members. The coaptation members may be differ based on the artificial body. The coaptation members may have different bridge configurations. The coaptation members may be of different sizes. The coaptation members may have different lengths. The kit may further include a measuring device structured to measure a size of an orifice of the valve.

In some embodiments, the disclosure may relate to a method for repairing a heart valve. The method may include implanting a heart valve device surgical implant device for a heart valve of a patient. The implanting may be performed using surgical, minimally invasive or percutaneous techniques. In other embodiments, the implanting may be performed using traditional open-heart surgical techniques. In some embodiments, the implanting may include loading the device onto a delivery catheter. The device may include may include an artificial body having a surface structured to receive the native valve leaflets; and a frame. In some embodiments, the method may include adjusting the artificial body after the implanting. The adjusting may include adjusting the expansion of the artificial body.

BRIEF DESCRIPTION OF THE DRAWINGS

The disclosure can be better understood with the reference to the following drawings and description. The components in the figures are not necessarily to scale, emphasis being placed upon illustrating the principles of the disclosure.

DETAILED DESCRIPTION OF THE EMBODIMENTS

Figure 1:
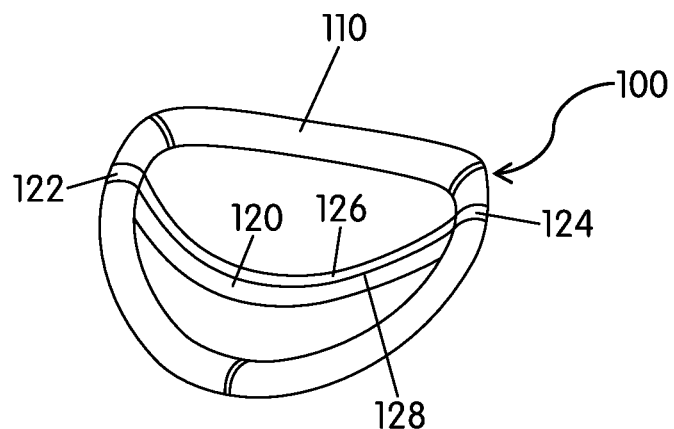
FIG. 1 shows an embodiment of a surgical valve implant device for a mitral valve.

The disclosed devices and methods specifically address the patient variability in heart valve structure, function and the need for beating heart adjustable devices that conform to the desired shape in individual patients at the time of surgery, acutely after surgery or several years after surgery. It will be understood that the devices disclosed, unless otherwise noted, may be implanted in patients undergoing first-time surgery; or these devices can be implanted in patients who had a failure of a previous repair. Also, unless otherwise noted, the devices disclosed may be implanted using surgical, minimally invasive or percutaneous techniques or using traditional open-heart surgical techniques. These devices are structured to be implanted into the cardiac structure under image guidance, repositionable during implantation, and retrievable immediately or several years after surgery.

The disclosed devices may reduce or eliminate regurgitation by enabling the overlap of the native valve leaflets onto each other or onto an artificial surface that is conformable to a desired shape as determined by the user at the time of implantation or at a time after implantation. The devices may also eliminate any blood leakage through the valve by sealing the orifice created by the non-coaptation of the leaflets. The shape may be determined based on the anatomy of the valve as determined by medical imaging devices. The placement of the device may also be confirmed by medical imaging devices. The medical imaging devices include but are limited to, ultrasound and echocardiogram.

These devices may be implanted percutaneously, using traditional open heart procedures, or minimally invasive procedures. The devices may be used and structured specifically for the mitral, tricuspid, aortic and pulmonary valves. The devices may be implanted, for example, via trans-femoral or transapical approach.

Unless otherwise noted, the frames (including the annuloplasty rings) of the surgical valve implant devices according to the disclosed embodiments below, may be formed of a semi-flexible material. For example, the frames may be made of a memory alloy that can conform to the desired shape upon implantation into the heart. The alloy may be, but is not limited to, Nitinol (also known as nickel titanium). Additionally, unless otherwise noted, the bridges of the surgical valve implant devices of the surgical valve implant devices according to the disclosed embodiments below, may be made of a rigid or semi-flexible material. The bridges may be also be made of a memory alloy that can conform to the desired shape upon implantation into the heart. The alloy may be, but is not limited to, Nitinol. In some embodiments, the frames may include inner tubing structured to inflate the frame, the artificial body, or a combination thereof.

The surgical valve implant devices may be modified according to the anatomy of the valve, and more specifically, the leaflets or the gap formed between the two leaflets. The embodiments of the devices structured for a mitral valve may also apply to a tricuspid valve or other valves. Also, the embodiments of the devices structured for the mitral and tricuspid valves may also apply to aortic and pulmonary valves. The devices may be structured to the type of valve deficiency.

FIGS. 1-20 illustrate surgical valve implant devices structured for a valve in which leaflets do not properly coapt and there may be a gap between the leaflets.

In some embodiments, the surgical valve implant devices may include a frame. In some embodiments, the frame may be an annuloplasty ring with a rigid or semi-flexible bridge. The annuloplasty ring may have a fabric outermost layer in which silicone tubing may be disposed. The silicone tubing may also include a core material. The frame may encompass the entire valve annular circumference. The edges of the frame may be structured to be sutured to an annulus of a valve. The shape of the frame may be modified according to the shape of annulus of the valve.

In some embodiments, the devices may further include a coaptation member. The coaptation member may be structured to prevent leaflets from going into the left atrium. The coaptation member may also be structured to provide an artificial surface onto which the leaflets can coapt.

The coaptation member may include a bridge. The shape of the bridge may be based on the valve to be repaired. For example, the bridge for a mitral valve may extend from one side of the frame to the other side. The bridge for a tricuspid valve may extend from three points on the frame towards a center or middle point to form a y-like shape. The bridge may be formed of a flexible material or a semi-flexible material, for example, Nitinol. The bridge may also be formed of any biocompatible material, for example, a biocompatible metal. The bridge may be along the same plane as the frame and be parallel thereto. In some embodiments, the bridge may be curved. In some embodiments, the bridge may have uneven curvature. The bridge may be adjusted either before or after the implantation in the heart. For example, the curvature and shape in the apical-basal plane may be adjusted.

The coaptation member may further include at least one artificial body. The artificial body may be permanently fixed to bridge. The artificial body may provide artificial surface onto which leaflets of the valve may coapt. The artificial body may be modified or selected based on the anatomy of the artificial body. The artificial body may have a shape, for example, the length and cross-section, that corresponds to the anatomy of the leaflets. The artificial body may not extend along the entire length of the bridge. In other embodiments, the artificial body may have the same or different cross-sections along the length of the bridge. In some embodiments, the coaptation member may include more than one artificial body. Each artificial body may be the same, different, or a combination thereof. The artificial bodies may differ in shape and/or length. The coaptation member may include different portions onto which the different or same artificial bodies are mounted.

The coaptation member may be structured to be adjusted when implanted. The artificial body and/or bridge may be structured to have an adjustment of a depth or distance from an annulus of the valve when implanted. In other embodiments, the artificial body and/or bridge may include a curvature, the amount of curvature depending on the desired depth or distance from an annulus of the valve when implanted.

In some embodiments, the artificial body may be an inflatable member, like a balloon. In other embodiments, the artificial body may be a biocompatible nonporous material, for example, a felt-like material or metal material.

The coaptation member may be permanently or removably disposed on the frame. For example, the coaptation member may be attached to the frame via connectors. The connectors may be any known fastener, such as screws or a hook. The frame may also include complimentary connectors. For example, the frame may include indentations or grooves structured to receive the hooks, holes with complimentary threads, and the like.

Figure 18:
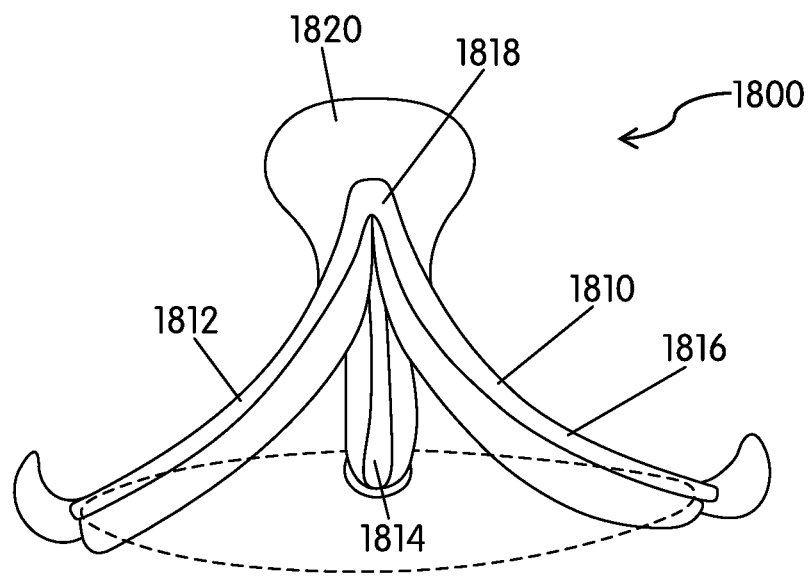
FIG. 18 shows an embodiment of a surgical valve implant device for an aortic valve and/or a pulmonary valve.
Figure 19:
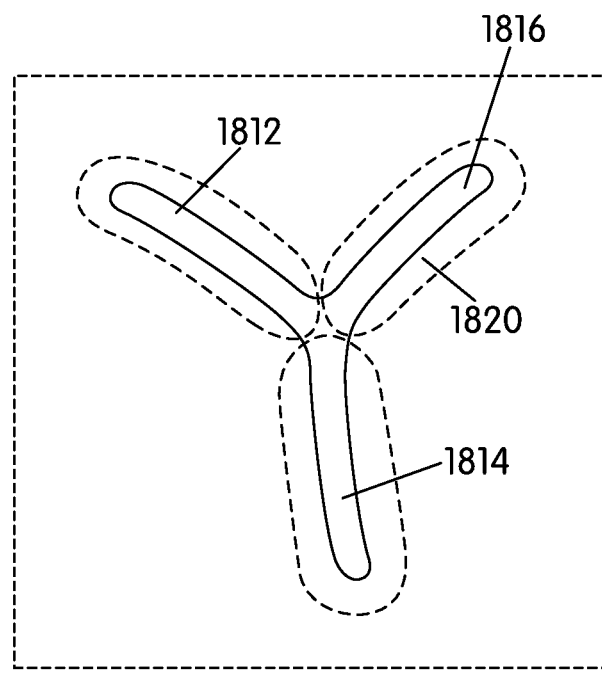
FIG. 19 shows another view of the surgical valve implant device.
Figure 20:
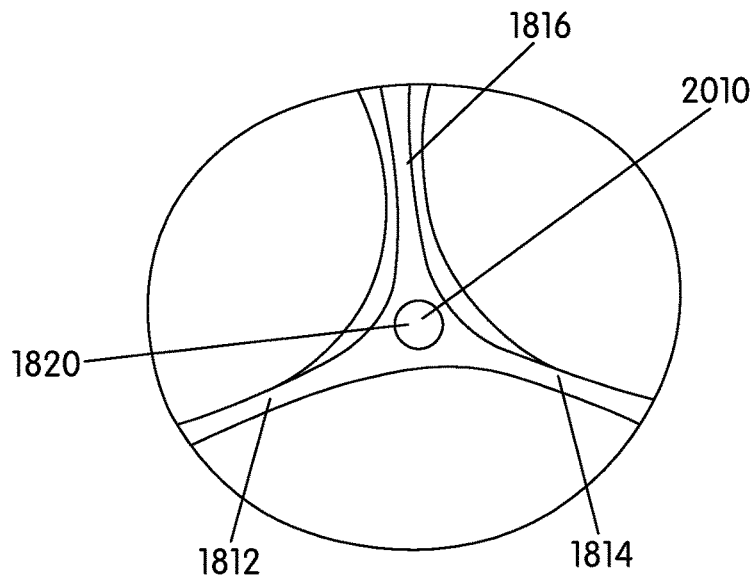
FIG. 20 shows a cross-sectional view of the surgical valve implant device.

FIGS. 1-9 show embodiments of surgical valve implant devices structured for a mitral valve. FIGS. 10-16 show embodiments of surgical implant devices structured for a tricuspid valve. FIGS. 18-20 show embodiments of surgical implant devices structured for aortic and pulmonary valves. It will be understood that the features of the frames and coaptation members may be included any one of the devices.

Figure 2:
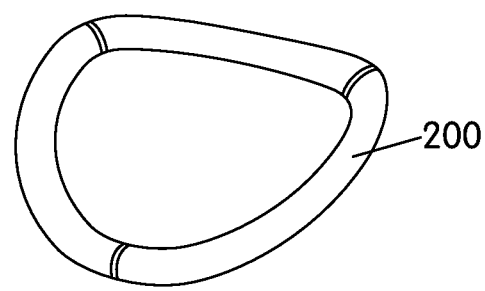
FIG. 2 shows an embodiment of a frame.

FIG. 1 shows a surgical valve implant device configured for a mitral valve. As shown in FIG. 1, a device 100 may include a frame 110. FIG. 2 shows an example of a frame 200.

The device 100 may further include a coaptation member 120. The coaptation member may have a shape that corresponds to the anatomy of the valve. For example, the coaptation member 120 may be structured for the mitral valve. The coaptation member 120 may include a bridge 126 that may extend from commissure to another of the valve.

The coaptation member 120 may further include at least one artificial body 128. The artificial body 128 may be structured to provide an artificial surface onto which leaflets may coapt.

In some embodiments, the coaptation member 120 may be integral with the frame 110. In other embodiments, the coaptation member 120 may be structured to be removable from the frame 110. The coaptation member 120 may include connectors 122 and 124. The frame 110 may further include complimentary connectors.

Figure 3:
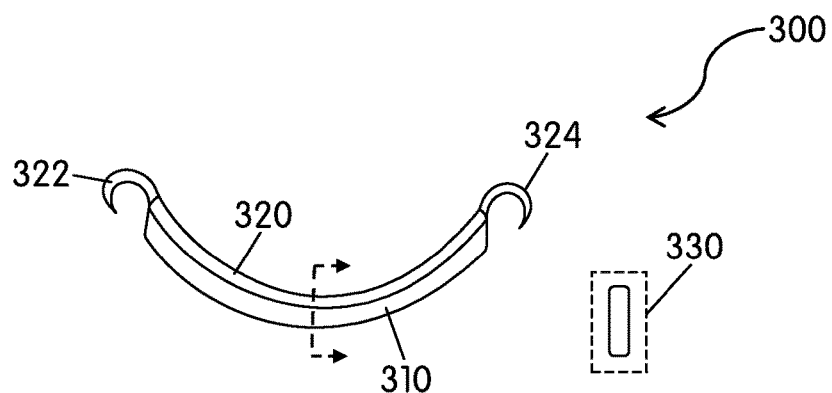
FIG. 3 shows an embodiment of a coaptation member.

FIGS. 3-9 show examples of a coaptation member. FIG. 3 shows an example of a coaptation member 300. The coaptation member 300 may have a frame 320 and connectors 322 and 324. The coaptation member 300 may further include artificial body 310. The artificial body 310 may have a cross-section 330. The artificial body 310 may have a rectangular shape along the entire length.

Figure 4:
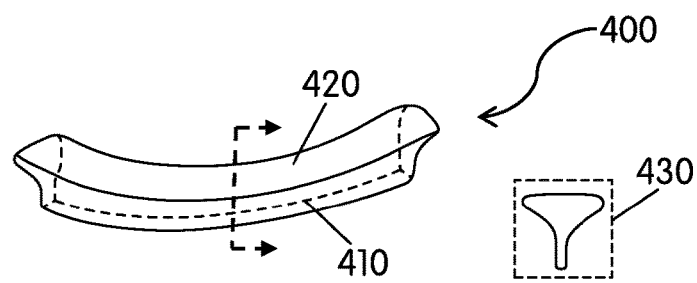
FIG. 4 shows another embodiment of a coaptation member.

In other embodiments, the artificial body may have an asymmetric cross-section. In some embodiments, the artificial body may have a tapered shape. FIGS. 4 t 6 show examples of coaptation members having tapered artificial bodies.

As shown in FIG. 4, a coaptation member 400 may include an artificial body 410 that has a tapered shape. The surface of the artificial body adjacent to the bridge 420 may have a diameter larger than the opposing surface as shown in cross-section 430.

Figure 6:
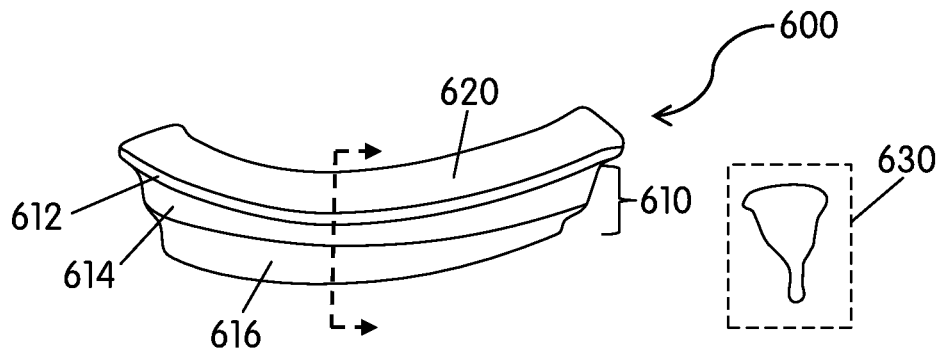
FIG. 6 shows another embodiment of a coaptation member.

In other embodiments, the artificial body may have a more gradual tapered shape. As shown in FIG. 6, a coaptation member 600 may include an artificial body 610. The artificial body 610 may include more than one portion. The artificial body 610 may include a first portion 612, a second portion 614, and a third portion 616. The first portion 612 may be adjacent to the bridge 620. The first portion 612 may have the largest diameter. The second and third portions 614 and 616 may have gradually smaller diameters.

Figure 5:
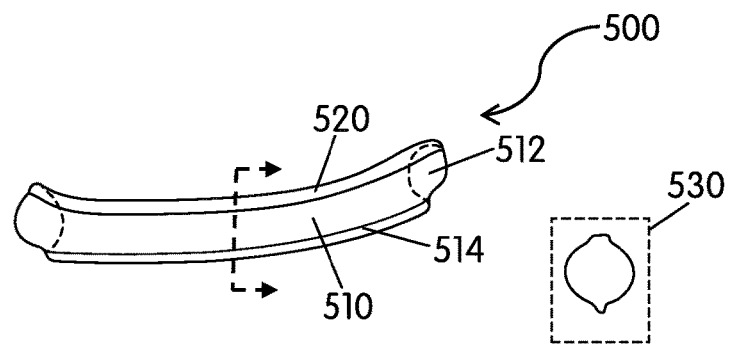
FIG. 5 shows another embodiment of a coaptation member.

In other embodiments, the artificial body may have a circular shape. FIG. 5 shows an example of a coaptation member 500. The coaptation member 500 may include an artificial body 510 that may include more than one portion. The artificial body 510 may include a first portion 512 that has a circular shape. The artificial body 510 may further include a second portion 514. The second portion may be a strip 514 that extends along all or part of the first portion 512. The second portion may be of a diameter that is significantly smaller than the diameter of the first portion, as shown in cross-section 530. The first portion 512 may be adjacent to the bridge 520 and the second portion 514 may be disposed on the opposing surface.

Figure 7:
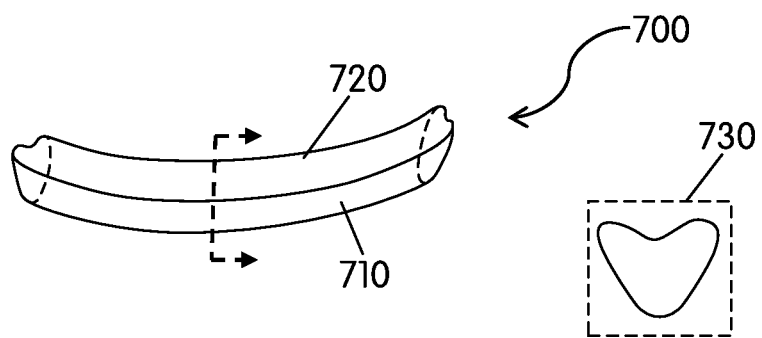
FIG. 7 shows another embodiment of a coaptation member.

In some embodiments, the artificial body may have a curved shape. FIG. 7 shows an example of a coaptation member 700. A coaptation member 700 may include an artificial body 710 with a curved shape, as shown in a cross-section surface 730. The coaptation surface 730 may have the smallest diameter furthest from a frame 720.

Figure 8:
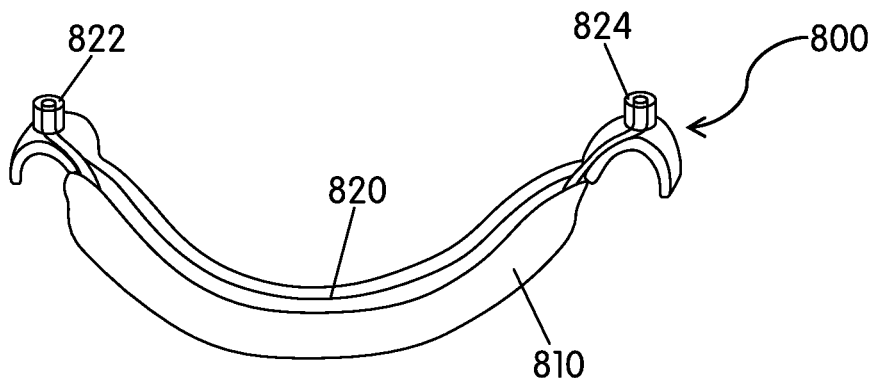
FIG. 8 shows another embodiment of a coaptation member.
Figure 9:
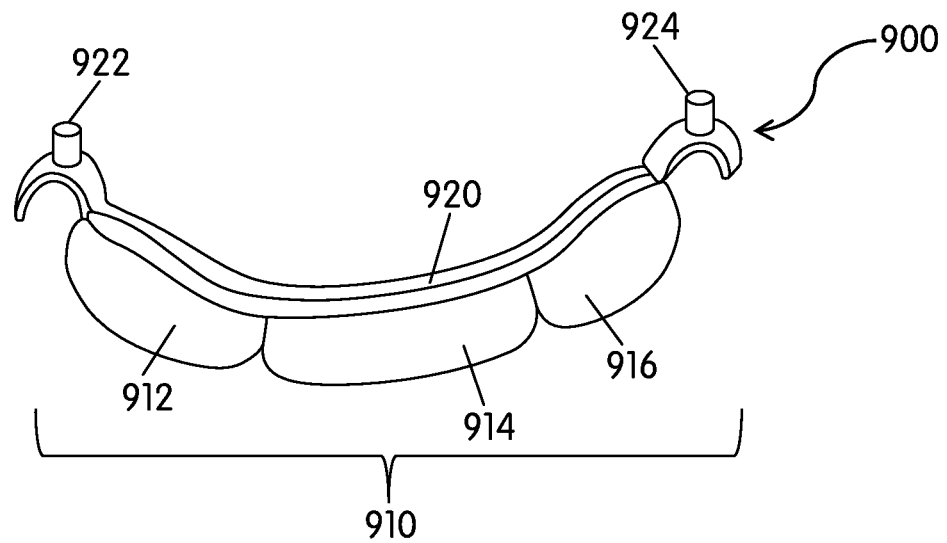
FIG. 9 shows another embodiment of a coaptation member.

In some embodiments, the artificial body may be structured to be adjustably expanded by adjusting the inflation. The artificial body may be adjusted before or after implantation into the heart. The artificial body may be adjusted in size intra-operatively or percutaneously using a catheter. The artificial body may be an inflatable member. The inflatable member may be a balloon. The coaptation member may include one inflatable member. In other embodiments, the coaptation member may include more than one inflatable member, for example, two, three, four, or more than four inflatable members. Each of the members may have a same shape, a different shape, or a combination thereof FIGS. 8 and 9 show examples of a coaptation member having an artificial body that is structured to be inflated. The inflatable members may have a cross-section as shown in FIGS. 3 through 7.

In some embodiments, the coaptation member may include a mechanism to controllably inflate and/or deflate the inflatable member(s) on the bridge. The coaptation member may include one or more than one mechanism. The mechanism may be a port. The coaptation member may any number of mechanisms; for example, the member may include one or two mechanisms. The mechanisms may be structured to controllably inflate and deflate the inflatable member(s) with a fluid, for example, saline. The inflatable member(s) may be individually or collectively adjusted and inflated. The inflation of the inflatable members may be adjusted to correspond to uneven curvatures of the patient's valve anatomy.

FIG. 8 shows an example of a coaptation member 800 with an inflated artificial body 810. The coaptation member 800 may include mechanisms 822 and 824 on the bridge 820 that are structured to adjustably expand the artificial body 810. The artificial body 810 is shown as including one inflatable member.

FIG. 9 shows an example of a coaptation member 900 including more than one artificial body 910. Each of the artificial bodies may be inflatable members. As shown in FIG. 9, the coaptation member 900 may include three inflatable members 912, 914 and 916 disposed on a frame 920 with mechanisms 922 and 924. Although the coaptation member is illustrated as having inflatable members, the coaptation member may include any number of inflatable members.

The surgical valve implant device shown in FIGS. 1-9 may be modified for the tricuspid valve. For example, the coaptation member of the device may modified to have a y-like shape to better correspond to the anatomy of the tricuspid valve, as shown in FIGS. 10-14. Otherwise, the components of the implant devices of FIGS. 10-14 may be similar to FIGS. 1-9, respectively.

Figure 10:
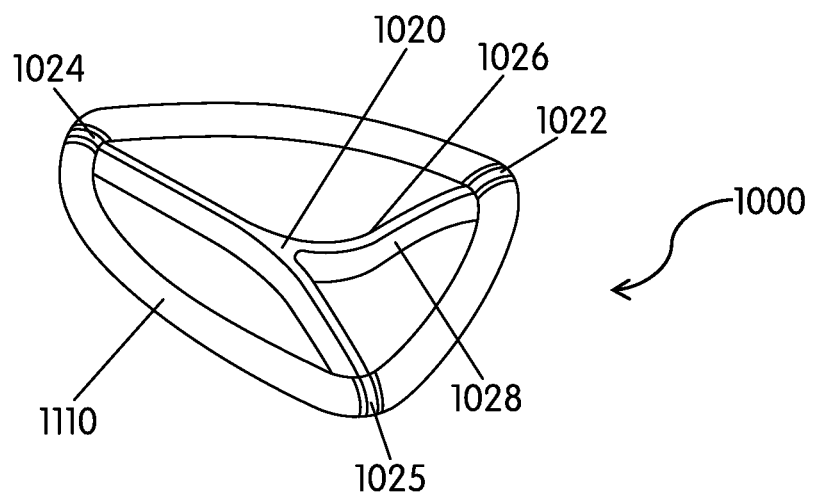
FIG. 10 shows an embodiment of a surgical valve implant device for a tricuspid valve.

FIG. 10 shows an example of a surgical valve implant device 1000 configured for a tricuspid valve. The device 1000 may include a frame 1110. Like the frame 110 of FIG. 1, the frame 1100 may be an annuloplasty ring with a rigid or semi-flexible bridge. The annuloplasty ring may have a fabric outermost layer in which silicone tubing may be disposed. The silicone tubing may also include a core material. The frame may encompass the entire valve annular circumference.

The device 1000 may further include a coaptation member 1020. The coaptation member may have a shape that corresponds to the anatomy of the valve. For example, the coaptation member 1020 may be structured for the tricuspid valve. The coaptation member 1020 may include a bridge 1026 that may extend from three different points on the frame and converge at a center point, so as to have a y-like shape. The coaptation member 1020 may further include at least one artificial body 1028. The artificial body 1026 may provide an artificial surface onto which leaflets of the valve may coapt. Like the artificial body of FIGS. 1-9, the artificial body 1028 may be an inflatable member, like a balloon. In other embodiments, the artificial body 1028 may be a biocompatible nonporous material, for example, a felt-like material or metal material.

In some embodiments, the coaptation member 1020 may be integral with the frame 1010. In other embodiments, the coaptation member 1020 may be structured to be removable from the frame 1010. The coaptation member 1020 may include connectors 1022, 1024, and 1025. In some embodiments, the connectors may be curved rings like hooks that are structured to firmly grasp the frame. In other embodiments, the connectors may be fasteners, like screws. The frame 1010 may further include complimentary connectors. In some embodiments, the complimentary connectors may be indentions, grooves, or bolts.

Figure 11:
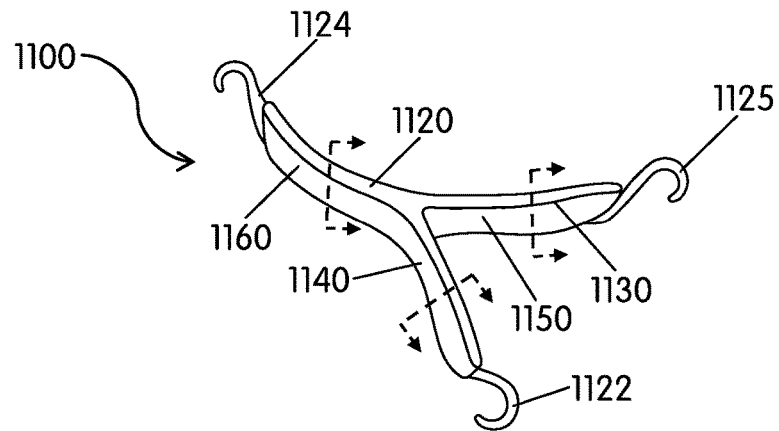
FIG. 11 shows an embodiment of a coaptation member.
Figure 12:
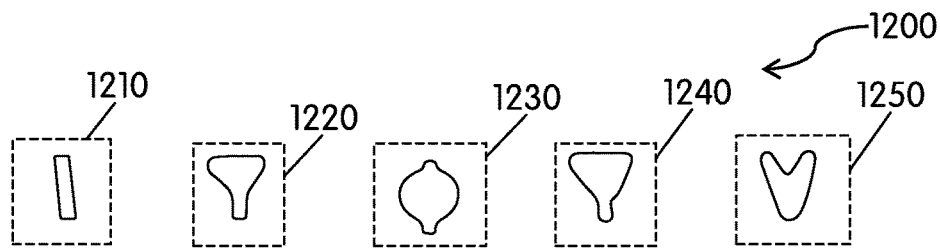
FIG. 12 shows embodiments of a coaptation member.
Figure 13:
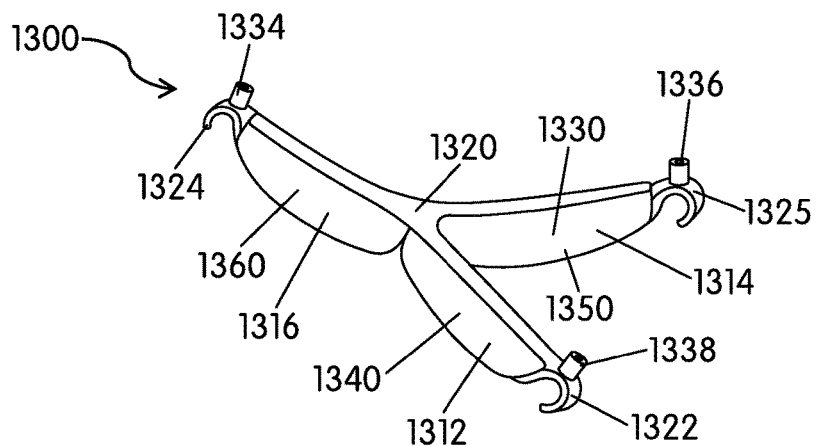
FIG. 13 shows an embodiment of a coaptation member for a tricuspid valve.

FIGS. 11-13 show examples of a coaptation member. FIG. 11 shows an example of a coaptation member 1100. The coaptation member 1100 may have a frame or bridge 1120 and connectors 1122, 1124, and 1125. The coaptation member 1100 may three portions. The artificial body may include a first portion 1140, 1150, and 1160. The artificial body 1130 provided on each portion may be the same, different, or a combination thereof. The cross-section may be the same or different as shown in the previous figures.

FIG. 12 shows an example of cross section 1200. The artificial body may have a rectangular cross-section 1210. In other embodiments, the artificial body may have a tapered or asymmetric cross-section, as shown in cross-sections 1220, 1230, 1240, and 1250. These cross-sections may be similar to cross-sections 330, 430, 530, 630, and 730, shown in FIGS. 3-7, respectively.

Like the mitral valve, in some embodiments, the device may include an artificial body that is structured to be adjustable. The artificial body may be structured to be inflated. An example of a coaptation member 1300 is shown in FIG. 1300. The coaptation member may include three portions 1340, 1350, and 1360 that converge at a center point. The portions may be of the same length or a different length. The length(s) may depend on the anatomy of the valve.

In some embodiments, the coaptation member 1100 may include a bridge or frame 1320. The frame may include connectors 1322, 1324, and 1325. The coaptation member 1300 may further include mechanisms 1334, 1336, and 1328 on the bridge 1320 adjacent to a respective connector. The coaptation member may include a single inflatable member or may include more than one inflatable member. The coaptation member may include an inflatable member provided on each portion. The member 1300 may include three inflatable members 1312, 1314 and 1316 disposed on a bridge 1320 with mechanisms 1334, 1336, and 1338. Although the bridge is illustrated as having three inflatable members, one on each portion of the bridge, the bridge may have any number of inflatable members. The inflatable members may have the same or different shape and size.

Figure 14:
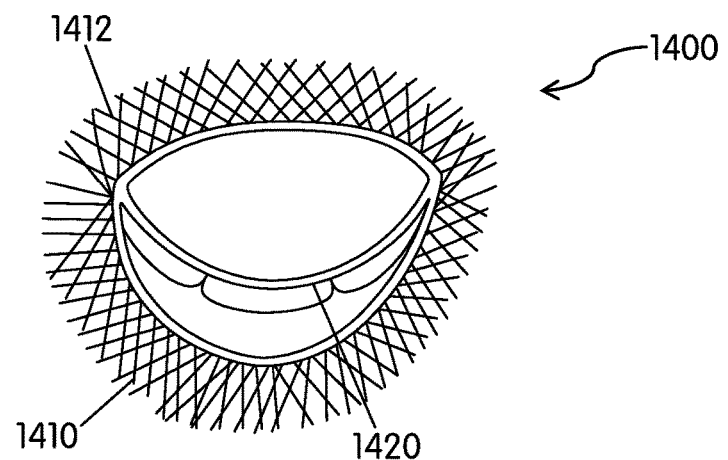
FIG. 14 shows an embodiment of a surgical valve implant device for a mitral valve.
Figure 15:
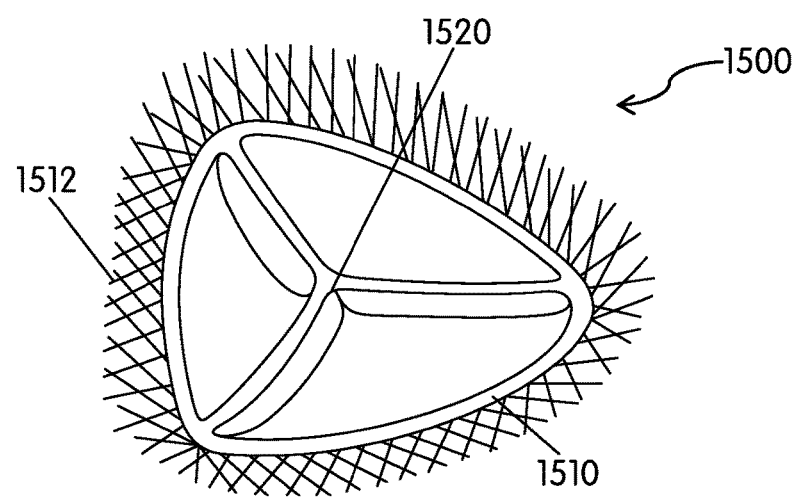
FIG. 15 shows an embodiment of a surgical valve implant device for a tricuspid valve.
Figure 16:
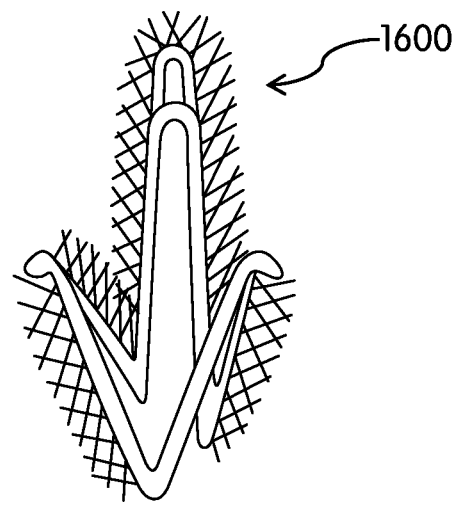
FIG. 16 shows an embodiment of a surgical valve implant device in a folded or collapsed position.

According to other embodiments, the frame may be a flexible frame. The frame may be structured to expand (open) and to collapse (close) into a smaller device. The frame may also include mesh. FIGS. 14-16 show an example of a device for a mitral and tricuspid valves. FIG. 14 illustrates a device 1400 in an expanded state for a mitral valve. The device 1400 may include a flexible frame 1410. The frame may further include a mesh 1412 that extends or protrudes from the frame 1420. The device may further include a coaptation member 1420 according to any of the embodiments.

FIG. 15 illustrates a device 1500 in an expanded, open state or unfolded for a tricuspid valve. The device 1500 may include a flexible frame 1510. The frame may further include a mesh 1512 that protrude from the frame 1510. The device may further include a coaptation member 1520 according to any of the embodiments.

FIG. 16 illustrates an example of a device 1600 in a collapsed or closed position. In the folded or collapsed position, the device may be loaded onto a catheter for implantation into a heart valve using minimally-invasive techniques. The device, when in a folded position, may be structured to be loaded onto a catheter so that it may be implanted into a heart valve.

Figure 17:
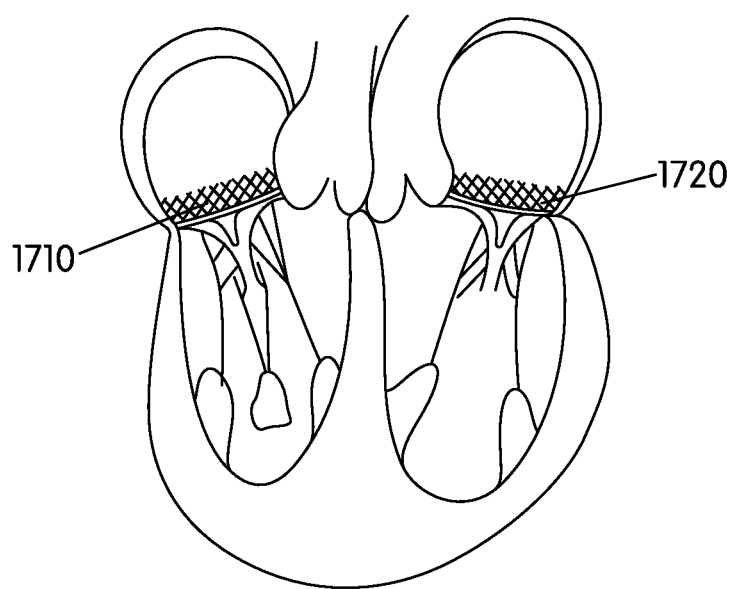
FIG. 17 shows surgical valve implant devices according to embodiments implanted into valves.

FIG. 17 shows an example of mitral and tricuspid devices according to embodiments implanted in a mitral valve 1720 and a tricuspid valve 1710, respectively.

FIGS. 18-20 show examples of surgical implant devices structured for aortic and/or pulmonary valves. The devices may be structured to be collapsed so that it can be loaded and delivered via a catheter-based device into an aortic valve or a pulmonary valve. The device may be delivered through tranfermal or transapical access and may be implanted into the valve annulus and commissures.

As shown in FIG. 18, a device 1800 may include a frame 1810. The frame 1800 may include three extensions 1812, 1814, and 1816. The three extensions may extend from a point 1818. The device 1800 may further include an artificial body 1820. The artificial body 1820 may surround completely or partially the frame 1810. The artificial body may include inflatable members or may be a nonporous material like the devices discussed with respect to the mitral and tricuspid valves. The artificial body may have the same or different shapes along each extension. FIGS. 19 and 20 show different view of FIG. 18.

The frame may be self-expanding and may be structured to be implanted into the native valve with good radial force. The device may have any number of inflatable members. As shown in FIG. 18, the device may have four inflatable members. There may be an inflatable member on top of the frame and along each of the three extensions. The inflation of the inflatable member may be adjusted according to the anatomy of the patient's valve. The inflatable member may be inflated individually or collectively. Although not shown, the frame may include a mechanism, such as a port, to receive fluid to inflate the inflatable member.

The inflatable members along each of the three extensions may come together to form a gap 2010 as shown in FIG. 2000. The inflatable members on top of the frame may be structured to seal the gap so as to eliminate any blood leakage.

According to embodiments, the devices may also be structured to prevent the leaflets from prolapsing into the heart chamber during contraction in addition to providing a coaptation surface. FIGS. 21-31 show devices according to these embodiments. The devices may include a frame and an artificial body. The frame may include one or two portions. The frame and artificial body may include any of the features discussed above with respect to FIGS. 1-20.

Figure 21:
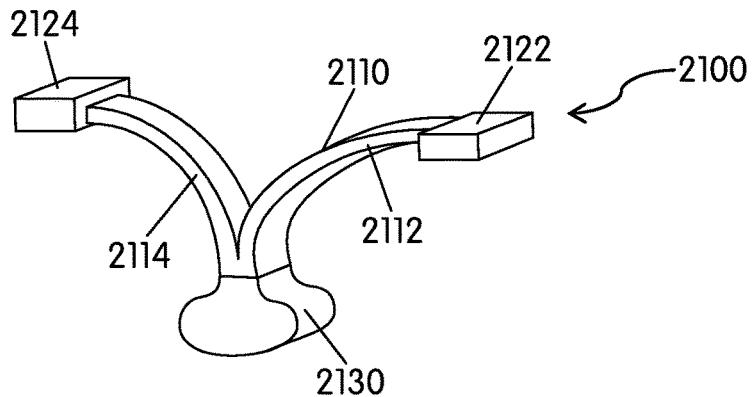
FIG. 21 shows an orthogonal view of surgical valve implant device according to other embodiments

FIG. 21 shows an orthogonal view of a surgical valve implant device 2100. The device 2100 may include a frame 2110. As shown in FIG. 21, the frame may include two portions 2112 and 2114. If the frame includes two portions 2112 and 2114 like shown in FIG. 21, the portions converge so that the device has a y-like shape. The frame may also include one portion. The frame may be solid or may include a hollow space(s) structured to allow blood flow. The frame may include any number of hollow spaces, e.g., one, two, three, more than three, and etc. The portions of the frame may have the same or different design.

Figure 29:
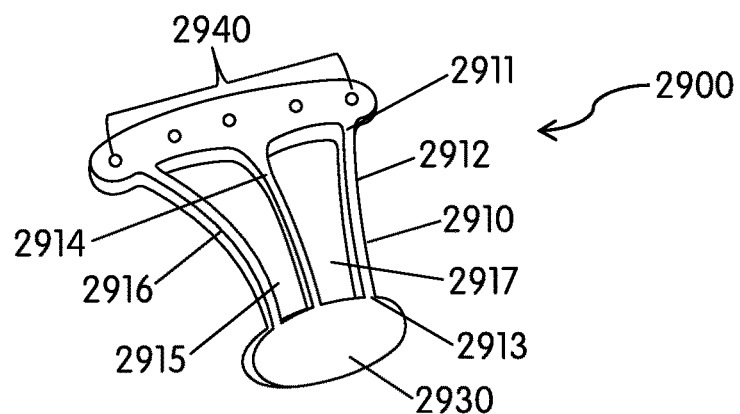
FIG. 29 shows a surgical valve implant device for a heart valve according to embodiments.

FIG. 29 shows an example of a device 2900. The device 2900 may include a frame 2910 with two hollow spaces 2915 and 2917. The device 2900 may include more or less spaces. The hollow spaces may between extensions 2912, 2914, and 2916 of the frame 2910. The extensions may extend from the top 2911 of the frame towards the bottom 2913 of the frame disposed near the artificial body 2930. The frame is not limited to the one portion shown in FIG. 29, and may include another portion of the same or different design.

Figure 31:
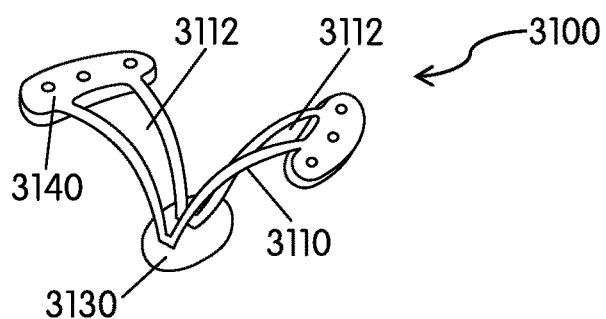
FIG. 31 shows a surgical valve implant device for a heart valve according to embodiments.

In some embodiments, the frame may be structured to be sutured to a valve. As shown in FIG. 21, the device 2100 may include platforms 2122 and 2124. The platforms may include a plurality of openings 2940 for sutures, for example, as shown in FIG. 29. An example of a device is shown in FIG. 31. As shown in FIG. 31, a device 3100 may include only one space 3112 for each portion of the frame 3110 that is connected to an artificial body or coaptation member 3130. The device may further include openings 3140 disposed on each platform.

Figure 22:
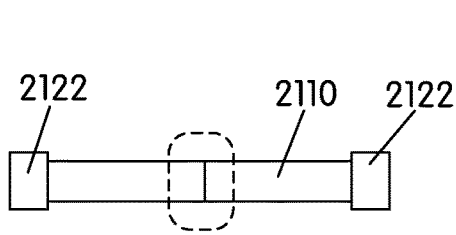
FIG. 22 shows a top view of the surgical valve implant device.
Figure 23:
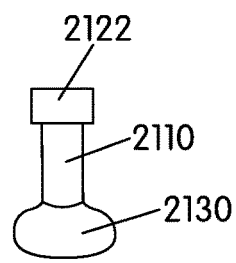
FIG. 23 shows a side view of the surgical valve implant device.

The device 2100 may include coaptation member 2130. The coaptation member may include an artificial body. The coaptation member may be fixedly disposed or removably disposed to one or both portions of a frame. The coaptation member may have a shape to correspond to the anatomy of the valve. The artificial body may have the same or different shape across the length of the coaptation member. FIGS. 22 and 23 show the top and side views of device 2100, respectively.

Figure 25:
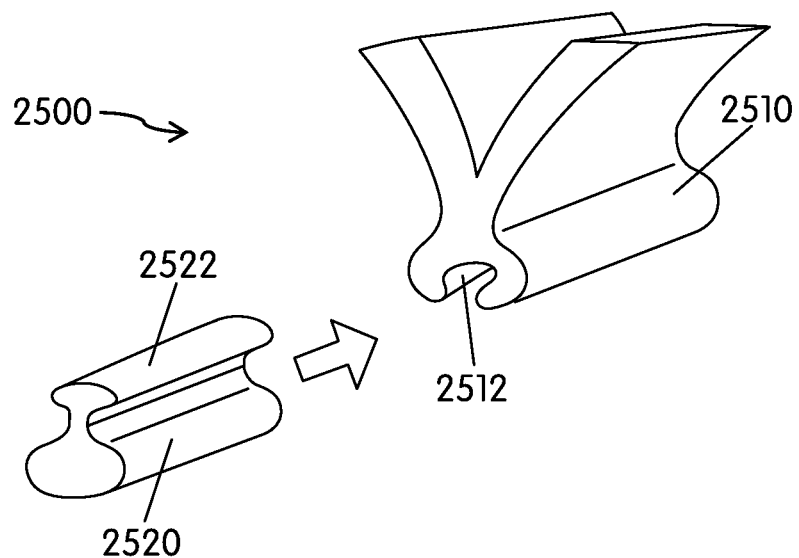
FIG. 25 shows a surgical valve implant device according to some embodiments.

FIG. 25 illustrates a device 2500 in which the coaptation member 2520 is detachable and removable from the frame 2510. The frame and the coaptation member may each include a connector. The connectors may be complimentary. For example, the frame 2510 may include connector 2512 that is structured to receive and fixedly dispose connector 2522 of the coaptation member 2520.

Figure 24:
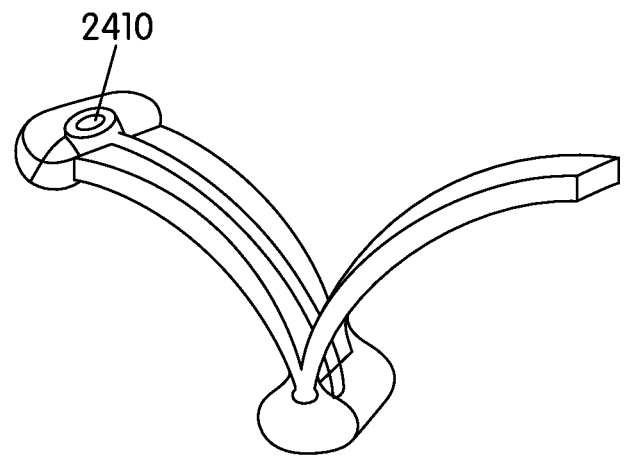
FIG. 24 shows an orthogonal view of a surgical valve implant device according to embodiments.
Figure 30:
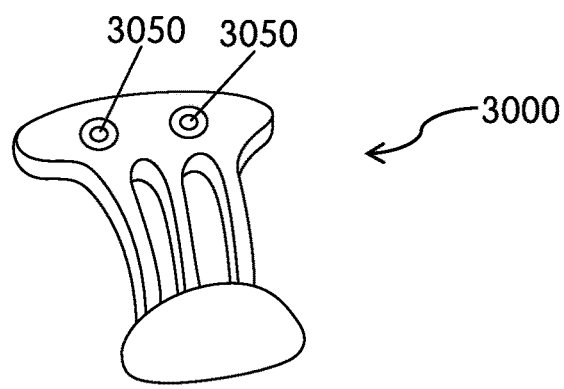
FIG. 30 shows a surgical valve implant device for a heart valve according to embodiments.

In some embodiments, the frame may further include a mechanism to receive fluid to inflate and deflate the artificial body. The mechanism may be for example, a port. The frame may include one or more than one mechanism, for example, a mechanism for one portion or for each portion. As shown in FIG. 24, the frame may include one mechanism 2410. The mechanism 2410 may be disposed on the platform. The frame may include two mechanisms 3050 on one portion, as shown in FIG. 30.

The inflatable member of the device may also be measured surgically using a measurement device prior to insertion. According to some embodiments, as shown, for example, in FIG. 28, the measurement device may be shaped such that two sliding elements 2810 and 2820 may slide along a ruler that allows measuring the size of the regurgitant orifice of the valve. In other embodiments, for example, for percutaneous methods, the regurgitant orifice area may be measured using 3D/2D echocardiography. The size of the inflatable member may then be chosen according to the measurements.

In some embodiments, the device may be directly implanted into the valve. In other embodiments, the device may be used with another device, for example, an annuloplasty ring, for implantation.

Figure 26:
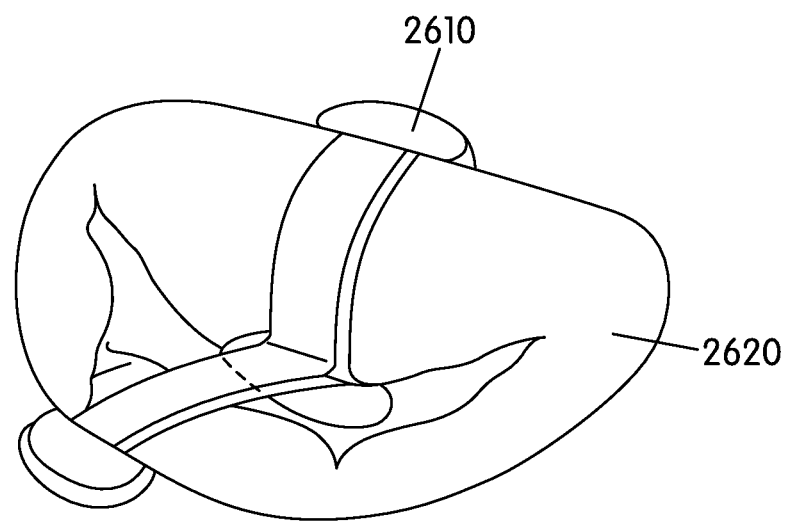
FIG. 26 shows a surgical valve implant device according to some embodiments implanted into a valve.
Figure 27:
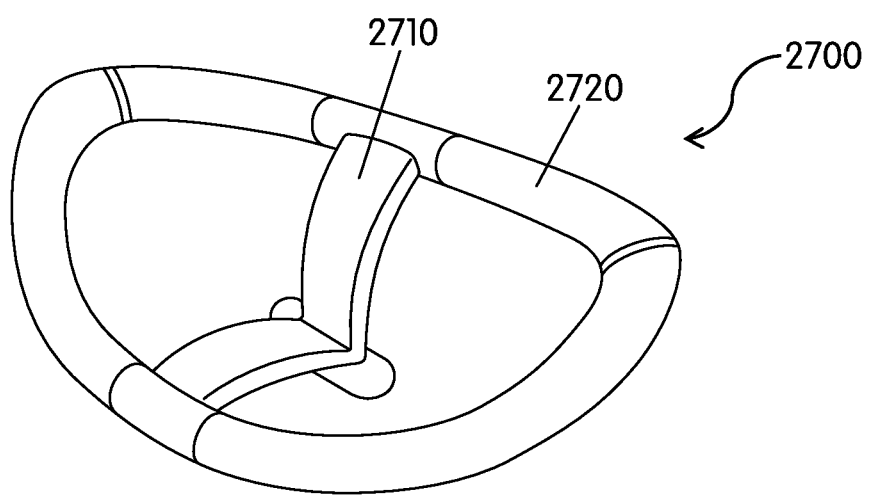
FIG. 27 shows a surgical valve implant device according to some embodiments implanted into a valve.
Figure 28:
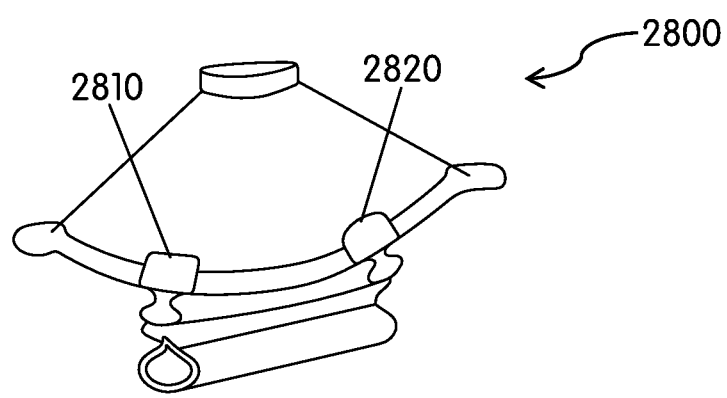
FIG. 28 shows an example of a measuring device according to an embodiment for use with the surgical valve implant device.

FIGS. 26 and 27 show example of the surgical implantation of the device. The device may be implanted to cover either the short axis or the long axis of the valve. In some embodiments, as shown in FIG. 26, the implant device 2610 may be implanted directly onto the regurgitant surface 2620. In other embodiments, as shown in FIG. 27, the implant device 2710 may be attached directly onto another frame 2720, for example a pre-existing annuloplasty ring, before being implanted into a valve According to some embodiments, one, some or all components of the devices may be structured for single use or be disposable. In some embodiments, one, some or all components may be sterilized. According to some embodiments, a portion or combination of the single use items may be sold as kit.

In some embodiments, the kit may include an implant device according to embodiments. The kit may include at least one frame and at coaptation member. In some embodiments, the kit may include a plurality of different coaptation members. The coaptation members may differ in shape. The coaptation members may also differ in shape and configuration of the artificial body. In further embodiments, the kit may further include a measuring device. In some embodiments, the kit may include a delivery device structured to deliver the device. In some embodiments, the kit may include a device configured to controllably inflate and deflate the artificial body.

While various embodiments of the disclosure have been described, the description is intended to be exemplary rather than limiting and it will be appeared to those of ordinary skill in the art that may more embodiments and implementations are possible that are within the scope of the disclosure.

What is claimed:

1. A device for repairing a heart valve having native valve leaflets, comprising:
   at least one artificial body having a length and having a surface structured to receive the native valve leaflets, the at least one artificial body being structured to be adjustable; and
   a bridge having a first end, a second end, and a length therebetween, the bridge being structured to adjust to a shape of the heart valve; and
   a frame,
   wherein the at least one artificial body is disposed on the bridge such that the entire length of the at least one artificial body is attached to the length of the bridge, and
   wherein the first end of the bridge is attached to a side of the frame and the second end of the bridge is attached to another side of the frame that opposes the side so that the bridge extends across the frame from the side of the frame to the other side.

2. The device according to claim 1, wherein the surface is structured so that when the at least one artificial body is implanted, the native valve leaflets coapt or rest during closure of the heart valve.

3. The device according to claim 1, wherein the at least one artificial body includes an inflatable member, and wherein the inflatable member is structured to be adjustable upon implantation in the heart valve.

4. The device according to claim 1, wherein the surface is structured to extend along a length of the overlap between the native leaflets.

5. The device according to claim 1, the device further comprising:
   wherein the bridge is made of a shape forming alloy material.

6. The device according to claim 1,
   wherein the bridge includes connectors structured to attach the bridge to the frame.

7. The device according to claim 1, wherein a combination of the artificial body and the frame is structured to control at least one leaflet of the heart valve from prolapsing and to be adjusted to a configuration such that the at least one leaflet overlap on the artificial body.

8. The device according to claim 1, wherein the at least one artificial body is structured to have an adjustment of a depth or distance from an annulus of the heart valve when implanted.

9. The device according to claim 1, wherein the at least one artificial body includes a curvature, an amount of the curvature depending on a desired depth or distance from an annulus of the heart valve when implanted.

10. The device according to claim 1, wherein the frame includes an annular ring.

11. The device according to claim 1, wherein the frame includes a connector disposed at one side and another connector disposed at an opposing side, the connector and the other connector configured to receive a first end of the bridge and a second end of the bridge so that the bridge extends across the frame.

12. The device according to claim 1, wherein the bridge is structured to be removably disposed with respect to the frame.

13. A device for repairing a heart valve of a heart of a patient having native valve leaflets, comprising:
   at least one artificial body having a length and having a surface structured to receive the native valve leaflets, the at least one artificial body being structured to be adjustable;
   a bridge having a first end, a second end, and a length therebetween, the bridge being structured to be adjusted, the at least one artificial body being disposed on the bridge such that the length of the at least one artificial body extends along the length of the bridge; and
   a frame,
   wherein the first end of the bridge is configured to attach to a side of the frame and the second end of the bridge is configured to attach to another side of the frame that opposes the side so that the bridge extends across the frame from the side of the frame to the other side of the frame,
   wherein the frame has a circular shape.

14. The device according to claim 13, wherein the bridge is structured to be removably disposed with respect to the frame.

15. The device according to claim 13, wherein the at least one artificial body includes at least one inflatable member, the at least one inflatable member being structured to be adjustable.

16. The device according to claim 13, wherein the bridge includes connectors structured to attach the bridge to the frame.

17. The device according to claim 13, wherein the bridge is made of a shape forming alloy material.

18. A device for repairing a heart valve having native valve leaflets, comprising:
   at least one artificial body having a length and having a surface structured to receive the native valve leaflets, the at least one artificial body being structured to be adjustable;
   a bridge having a length, the bridge being structured to adjust to a shape of the heart valve,
   a frame including a connector disposed at one side and another connector disposed at an opposing side,
   wherein the at least one artificial body is disposed on the bridge such that the entire length of the at least one artificial body is attached to the length of the bridge, and
   wherein the bridge is structured to be removably disposed with respect to the frame,
   wherein the bridge includes connectors that are structured to attach the bridge and the artificial body to the frame and complimentary to the connector and the other connector of the frame,
   wherein the bridge is connected to the frame so that the bridge and artificial body extend across from the one side of the frame to the opposing side of the frame.

19. The device according to claim 18, wherein the bridge is made of a shape forming alloy material.

20. The device according to claim 18, wherein the frame includes an annular ring and wherein the bridge is structured to be removably disposed with respect to the frame.

* * * * *